United States Patent
Shenoi et al.

(10) Patent No.: US 8,960,026 B2
(45) Date of Patent: Feb. 24, 2015

(54) SAMPLE COLLECTION DEVICE

(75) Inventors: Hemanth Shenoi, Verona, WI (US); Mike Domanico, Middleton, WI (US); Graham Lidgard, Madison, WI (US); Joseph E. Schiestle, Waunakee, WI (US); Scott Castanon, Carlsbad, CA (US); Keith Kopitzke, Fallbrook, CA (US); Martin Bouliane, Carlsbad, CA (US)

(73) Assignee: Exact Sciences Corporation, Madison, WI (US)

( * ) Notice: Subject to any disclaimer, the term of this patent is extended or adjusted under 35 U.S.C. 154(b) by 525 days.

(21) Appl. No.: 13/449,878

(22) Filed: Apr. 18, 2012

(65) Prior Publication Data
US 2012/0260748 A1    Oct. 18, 2012

Related U.S. Application Data

(60) Provisional application No. 61/476,707, filed on Apr. 18, 2011.

(51) Int. Cl.
*G01N 1/08*    (2006.01)
*A61B 10/00*   (2006.01)

(52) U.S. Cl.
CPC ............. *G01N 1/08* (2013.01); *A61B 10/0038* (2013.01)
USPC ........................................ 73/864.42

(58) Field of Classification Search
USPC .......................... 73/864.32, 864.42
See application file for complete search history.

(56) References Cited

U.S. PATENT DOCUMENTS

| | | | | |
|---|---|---|---|---|
| 2,362,090 A * | 11/1944 | Peters | | 73/864.44 |
| 2,914,950 A * | 12/1959 | Giguere | | 73/864.42 |
| 3,636,954 A | 1/1972 | Weston | | |
| 3,949,497 A * | 4/1976 | Crump | | 37/340 |
| 5,440,942 A * | 8/1995 | Hubbard | | 73/864.91 |
| 5,517,868 A * | 5/1996 | Turriff et al. | | 73/864.44 |
| 6,098,724 A * | 8/2000 | Ricker | | 175/20 |
| 7,571,658 B1 * | 8/2009 | Elliott | | 73/864.42 |
| 2010/0121046 A1 * | 5/2010 | Ahlquist et al. | | 536/25.41 |

FOREIGN PATENT DOCUMENTS

DE    4244504    *    5/1993

* cited by examiner

*Primary Examiner* — Robert R Raevis
(74) *Attorney, Agent, or Firm* — Casimir Jones S.C.

(57) ABSTRACT

Provided herein is technology relating to collecting samples of soft matter compositions, and particularly, but not exclusively, to devices and methods for collecting stool samples.

16 Claims, 10 Drawing Sheets

SAMPLE COLLECTION DEVICE

The present application claims the benefit of U.S. Provisional Patent Application Ser. No. 61/476,707, filed Apr. 18, 2011, which is incorporated by reference in its entirety.

FIELD OF INVENTION

Provided herein is technology relating to collecting samples and particularly, but not exclusively, to devices, methods, systems, and kits for collecting stool samples.

BACKGROUND

Producing a defined volume or mass of a sample for subsequent testing is an important initial step in many settings, e.g., in the food industry, for environmental monitoring, in medicine, etc. For instance, in the medical clinic, laboratory examination of fecal samples is an important component of some diagnoses. In these cases, stool specimens are taken from a patient and examined for conditions relative to the health or ailment of the patient. As specific examples, physicians and clinicians often test stool samples as a component of testing for colon or rectal cancer or pre-cancerous conditions, or to identify bacteria or viruses that may be involved in an infection. Additionally, some diagnostics require isolating and assaying nucleic acids, proteins, fats, or other analytes present in the stool specimen. Such tests for viruses, bacteria, nucleic acids, proteins, and fats are also performed on other types of samples, e.g., food and environmental samples. Consequently, acquiring a sample from a specimen (e.g., a stool specimen) is the first step in sample processing for many tests (e.g., the medical diagnostic analysis of feces). As the first step in such analyses, the sample integrity, the reproducibility of the sample size, the reproducibility of the means and method used to acquire the sample, and the efficiency of sample preparation are all critically important for the subsequent processing and testing steps.

The collection of some samples (e.g., fecal samples) for testing presents particular challenges, both to the individuals providing such samples as well as to the technicians testing them. Samples obtained away from a medical facility or testing laboratory must be mailed or otherwise transported and, when received at a laboratory, need to be handled without exposing technicians to such sample material. The collected samples further need to be appropriately tested. There remains a need for better methods and devices for collecting such samples, transferring the samples to test devices, and performing assays, in particular to facilitate the transfer of a sample to a test device while minimizing the possibility of exposure of a technician to the sample.

Conventional sample collection devices and techniques have used, for example, buckets and spoons to prepare a sample from a larger specimen. For instance, for medical diagnostic tests of stool samples, entire stool specimens have been collected in buckets with lids, to which a bulk quantity of stabilization buffer is added. Spoon-type devices are used to break off samples from a specimen, which samples are then placed in a jar or tube with buffer. However, these and other conventional collection methods have proven unsatisfactory for a number of reasons. For example, collecting whole specimens in buckets does not provide samples of reproducible size or volume suitable for accurate and/or automated downstream processing. Manual weighing, aliquoting and/or dilution are required prior to processing, but these manipulations are not efficient, accurate, or sufficiently reproducible. Preparing a sample from a specimen with a spoon device is not as reproducible as using a fixed-volume device. Using a spoon also requires applying a downward pressure on the specimen. If the specimen has been collected in a disposable receptacle, e.g., a collection paper, downward pressure during sampling increases the probability that the underlying collection paper will fail. Moreover, using a spoon requires the person collecting the sample to be close to the specimen from which the sample is to be taken, increasing the risk of exposure. Moreover, most conventional devices for sample capture are non-intuitive to use, position the sample collection portion of the device near a user-manipulable portion of the device, and/or make it difficult for the user to place the collected sample into a container, such as a collection tube.

SUMMARY OF THE INVENTION

Accordingly, there is a need for a simple, inexpensive device that can be used to collect a sample from a larger specimen (e.g., a stool specimen). The size and/or weight of the sample gathered should be sufficiently reproducible with little or no user training, and sample acquisition should be easily achievable using one hand by people with poor vision and/or poor manual dexterity. Producing samples having a fixed, reproducible volume and/or mass is of particular importance for the accuracy and automation of subsequent downstream testing. Additionally, the sample needs to be collected in a manner that will not break or dislodge any specimen collection substrate on which the specimen has been previously collected (e.g., a commode-mounted collection paper holding a stool sample).

A sample collection device should be capable of opening widely to allow the collection surfaces ample room to be placed around a portion of a specimen, then to be closed to encompass a defined volume or mass of a sample. It is also preferable to keep the operational portion (i.e., the part(s) held and/or manipulated or operated by the user) of the device as far as reasonably possible from the specimen to reduce the chance of contaminating the sample by the person operating the device, and to minimize exposure of the person operating the device to the specimen and the sample. The device should also allow depositing the collected sample into a container, e.g., a tube containing a stabilization buffer, to facilitate subsequent processing and analysis.

Thus, provided herein is technology relating to collecting samples and particularly, but not exclusively, to devices, methods, systems, and kits for collecting and preparing samples of soft matter compositions, such as stool specimens, soft foods, etc. In some embodiments, a device is provided for collecting a sample, said device comprising a body and a detachable sample capsule attached to the body, wherein the detachable sample capsule comprises a sample collection space configured to enclose a sample. In some embodiments, the detachable sample capsule comprises a first half-scoop comprising a concave sample collection surface and a second half-scoop comprising a second sample collection surface opposed to the concave sample collection surface of the first half-scoop. In some embodiments, the second sample collection surface is concave. Some embodiments additionally provide an ejector mechanically connected to the detachable sample capsule, wherein, in some embodiments, manipulation of the ejector detaches the detachable sample capsule from the body.

The device is configured to encapsulate a sample within a sample capsule. While not limited with respect to the means by which the sample is introduced into the sample capsule, some embodiments provide that parts of the device move relative to one another to allow the device to be placed around a portion of a specimen and then to allow the device to encapsulate a portion of the specimen as a sample. Accordingly, some embodiments provide a device configured to move between an open and a closed state, wherein the open state comprises the body in a first state and the first half-scoop separated from the second half-scoop; and the closed state comprises the body in a second state and the first half-scoop in contact with the second half-scoop, wherein the concave sample collection surface of the first half-scoop and the sample collection surface of the second half-scoop form a sample collection space. Some embodiments provide that detaching the detachable sample capsule deposits the sample into a sample container (e.g., a 50-milliliter conical tube or other suitable container).

In some embodiments, it is desirable to maintain the sample within a secured sample capsule to facilitate sample handling and to prevent sample loss, contamination, or user exposure in subsequent sample handling. Thus, in some embodiments of the sample collection device, the device further comprises a clasp component to secure the article in a closed state. In some embodiments, a clasp component comprises a first clasp component and a second clasp component, wherein the first clasp component and the second clasp component engage to secure the article in the closed state. In some embodiments, the body comprises the first clasp component and the second clasp component and in some embodiments the first half-scoop comprises the first clasp component and the second half-scoop comprises the second clasp component such that the first clasp component and the second clasp component engage to secure the first half-scoop to the second half-scoop.

The sample capsule is not limited in its form or shape. Contemplated herein are shapes for the sample capsule that are spherical, cylindrical, rectangular, oblong, elliptical, etc. In some embodiments, the detachable sample capsule has a cylindrical shape. In specific embodiments, the cylindrical shape comprises a circular base and a height, wherein the circular base has a radius of approximately 1-2 centimeters and the height is approximately 2-3 centimeters. In some embodiments, the sample capsule comprises a sample collection space that is designed to hold a particular mass or volume of sample. The technology provided is not limited in the mass or volume of sample that can be accommodated within the sample collection space. For instance, in some embodiments, the sample collection space has a volume of about 0.5 to 5 cubic centimeters. In some embodiments, the sample collection space has a volume of about 5 to 10 cubic centimeters.

Some embodiments find advantages in constructing the device from various types of materials, e.g., disposable materials, recyclable materials, reusable materials, sterilizable materials, autoclavable materials, chemically inert materials, biodegradable materials, etc. As such, in some embodiments of the device, the body is made from a disposable material and in some embodiments the body is made from a reusable, sterilizable material. Furthermore, in some embodiments the detachable sample capsule is made from a disposable material and in some embodiments the detachable sample capsule is made from a reusable, sterilizable material. Bodies and detachable sample capsules of various construction and materials can be mixed and matched to provide a device most appropriate for the user's needs. In some embodiments a single body is configured to be used with a variety of different sample capsules, such that a particular type or volume of sample capsule may be selected for use as suitable for a particular sampling purpose.

In some embodiments, the device is configured for manual manipulation by a user. In some embodiments, the device is configured for manipulation by one hand, i.e., the user uses one hand to collect the sample and to deposit the sample into a sample collection tube.

In some embodiments of the device, the device takes the shape of a pair of tongs. Thus, in some embodiments, the body comprises a first operating member comprising a proximal end, a distal end, and a longitudinal axis; and a second operating member comprising a proximal end, a distal end, and a longitudinal axis, wherein the proximal end of the first operating member is mechanically connected to the proximal end of the second operating member to form a fulcrum and the first operating member, the second operating member, and the fulcrum form a third-class lever; the first half-scoop is attached to the distal end of the first operating member; and the second half-scoop is attached to the distal end of the second operating member. Some embodiments further comprise an ejector movably attached to the device, e.g., to the body, wherein a manipulation of the ejector detaches the detachable sample capsule from the body. Some embodiments provide that the manipulation comprises sliding the ejector along the longitudinal axis of the first member or sliding the ejector along the longitudinal axis of the second member. In certain embodiments, the ejector is configured to be inoperable when a capsule is not in a closed state. While not limited in the design or construction of the device to provide the particular embodied configuration, in some embodiments the device is made from a single piece of appropriate material, that is, a single manufacture comprises the first member and the second member.

In some embodiments, the device takes the shape of a scissors-type device comprising compound levers. Accordingly, in some embodiments, the body comprises a first compound lever comprising a first proximal operating member comprising a proximal end and a distal end and a first distal member comprising a proximal end and a distal end, wherein the first proximal operating member is a first-class lever and the first distal member is a first-class lever; a first joint connecting the distal end of the first proximal operating member to the proximal end of the first distal member; a second compound lever comprising a second proximal operating member comprising a proximal end and a distal end and a second distal member comprising a proximal end and a distal end, wherein the second proximal operating member is a first-class lever and the second distal member is a first-class lever; a second joint connecting the distal end of the second proximal operating member to the proximal end of the second distal member; a first common fulcrum for the first proximal operating member and the second proximal operating member; and a second common fulcrum for the first distal member and the second distal member, wherein the first half-scoop is attached to the distal end of the first distal member, the second half-scoop is attached to the distal end of the second distal member; and manipulation of the first proximal operating member and the second proximal operating member causes movement of the first half-scoop and the second half-scoop. In some embodiments, the device further comprises an ejector movably attached to the device, e.g., to the body, wherein a manipulation of the ejector detaches the detachable sample capsule from the body. In some embodiments, the first proximal operating member further comprises a first longitudinal axis and the second operating member further comprises a second longitudinal axis and the manipulation comprises sliding the ejector along a third longitudinal axis that approximately bisects the first longitudinal axis of the first proximal operating member and the second longitudinal axis of the second proximal operating member. In certain embodiments, the ejector is configured to be inoperable when a capsule is not in a closed state.

In some embodiments of the device, a sliding mechanism is used to capture a sample. Accordingly, in some embodiments the body comprises a frame comprising a proximal end, a distal end, and a longitudinal axis; and a slide movably attached to the frame, wherein the slide comprises a proximal end, a distal end, and a longitudinal axis, wherein the first half-scoop is attached to the distal end of the frame, the second half-scoop is attached to the distal end of the slide, a manipulation of the slide causes a movement of the second half-scoop relative to the first half-scoop, and the concave sample collection surface of the first half-scoop and the concave sample collection surface of the second half-scoop are maintained in a parallel opposition to each other. Some embodiments provided herein comprise an actuator. In some embodiments, the actuator is rotationally attached to the frame and in some embodiments a manipulation of the actuator moves the first half-scoop relative to the second half-scoop. While not limited in the form of the actuator, in some embodiments the actuator is a gear rotationally attached to the frame by an axle and the slide comprises gear teeth such that the gear engages the gear teeth of the frame to produce a rack and pinion mechanism. In some embodiments, the actuator comprises a first frictional surface rotationally attached to the frame by, e.g., an axle, and the slide comprises a second frictional surface such that the first and second frictional surfaces engage to produce a rack-and-pinion mechanism. Some embodiments provide for an ejector that is movably attached to the device, e.g., to the body, wherein a manipulation of the ejector detaches the detachable sample capsule from the body. In some embodiments the ejector moves along an axis perpendicular to the longitudinal axis of the frame and the longitudinal axis of the slide. In certain embodiments, the ejector is configured to be inoperable when a capsule is not in a closed state.

As described herein, the present technology provides a device for collecting a sample. Accordingly, some embodiments provide a device that is manipulated by manipulating the body to collect and secure the sample and manipulating the ejector to deposit the sample.

The device is not limited in the types, forms, compositions, or sizes of the specimen from which a sample is taken. Thus, in some embodiments the sample comprises soft matter. While the device is not limited to particular volumes or masses of sample, in some embodiments, the sample has a mass approximately equal to or greater than 4 grams and in some embodiments the sample has a mass approximately equal to or greater than 8 grams. Furthermore, the device is not limited in the source of the specimen to be sampled. For example, in some embodiments the sample is a stool sample. Some embodiments provide that the stool sample is from a human subject. It is contemplated that the device is easy to use by individuals who are not medical professionals or otherwise trained in clinical practices. Thus, in some embodiments, the stool sample is collected in the home of the human subject. In some embodiments the sample is a food sample and in some embodiments the sample is an environmental sample. While not limited in the types of samples that can be collected using the device, some examples are sputum, vomit, tissue, biopsy, necropsy, soft matter, soil, and sludge.

Also provided herein are methods related to collecting a sample in accordance with the technology provided herein. For example, embodiments of the technology provide methods of collecting a sample comprising the steps of positioning an embodiment of the devices provided herein so that the first half-scoop is placed on one side of the sample and the second half-scoop is placed on the other side of the sample, moving together the first half-scoop and the second half-scoop to encapsulate and capture the sample and depositing the first half-scoop, second half-scoop, and the sample into a sample container. In some embodiments of the methods provided, the positioning, moving, and depositing steps are performed using one hand. It is contemplated that the device is easy to use by individuals who are not medical professionals or otherwise trained in clinical practices. Thus, in some embodiments, the method is performed in the user's home to collect the sample that, in some embodiments, is a stool sample.

Some embodiments of the methods are related to embodiments of the devices provided above in which a sliding mechanism is used to capture a sample. Accordingly, in some embodiments the methods comprise the steps of positioning an embodiment of the devices provided above in which a sliding mechanism is used to capture a sample so that the first half-scoop is placed on one side of the sample and the second half-scoop is placed on the other side of the sample, moving together the first half-scoop and the second half-scoop to encapsulate and capture the sample, and depositing the first half-scoop, second half-scoop, and the sample into a sample container, wherein the concave sample collection surface of the first half-scoop and the concave sample collection surface of the second half-scoop are maintained in a parallel opposition to each other. In some embodiments, the sample is a stool sample.

Furthermore, provided herein are systems for collecting a sample comprising a sample collection device and a sample container, wherein the sample collection device is configured to encapsulate the sample within a detachable sample capsule and deposit the detachable sample capsule into the sample container, and wherein the sample container is configured to accept and contain the detachable sample capsule. In some embodiments of the system, the detachable sample capsule comprises a first half-scoop and a second half-scoop and the sample collection device is configured to move apart the first half-scoop and the second half-scoop and to move together the first half-scoop and the second half-scoop. In some embodiments of the system, the sample collection device comprises an ejector for detaching the detachable sample capsule. In certain embodiments, the ejector is configured to be inoperable when a capsule is not in a closed state. In some embodiments of the system, the sample is a stool sample and in some embodiments of the system the sample container contains a collection fluid. While not limited in the composition of the collection fluid (e.g., an aqueous or organic solution), in some embodiments the collection fluid comprises a buffer and in some embodiments the collection fluid comprises a preservative. In some embodiments the collection fluid comprises a composition that stabilizes an analyte present in the sample and inhibits the degradation of the analyte. In some embodiments, the system further comprises a specimen collecting system or device for collecting a larger specimen from which a sample is to be collected using a sample collection device. For example, in some systems for collecting stool samples, the system comprises a receptacle (e.g., a basket, a bucket, a collection paper, a "hat" receptacle, etc.) configured for convenient collection of an entire specimen from a patient or subject. In some embodiments, the receptacle is configured to be positioned and/or supported by a toilet, toilet seat, a commode, or bedpan, while in other embodiments, a receptacle is configured for use directly.

Also provided are kits for collecting a sample, the kits comprising a sample collection device comprising a detachable sample capsule and a sample container configured to contain the detachable sample capsule. In some embodiments, kits may also comprise one or more of a collection fluid, a specimen receptacle, and/or an instruction for use. While not limited in the composition of the collection fluid (e.g., an aqueous or organic solution), in some embodiments the collection fluid comprises a buffer and in some embodiments the collection fluid comprises a preservative. In some embodiments the collection fluid comprises a composition that stabilizes an analyte present in the sample and inhibits the degradation of the analyte. In some embodiments, kits may comprise packaging for shipping or mailing a collected sample. In some embodiments of the methods, systems, and kits provided herein, the sample container is a 50-milliliter conical tube.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 7 is a drawing showing an embodiment of a stool sample collection device.

FIG. 8 is a drawing showing the use of the stool sample collection device shown in FIG. 7.

DETAILED DESCRIPTION OF THE INVENTION

Provided herein is technology relating to collecting samples and particularly, but not exclusively, to devices, methods, systems, and kits for collecting stool samples.

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, "parallel opposition" describes the relative orientation of two objects such that they largely lie in parallel planes and the similar faces, features, etc. of each object are oriented toward each other. For example, the jaws of a vernier caliper and the jaws of a handscrew clamp are generally in parallel opposition to one another. Two objects move while maintaining parallel opposition when they move relative to each other along an axis mutually normal to the parallel planes within which the objects lie without substantially disturbing their largely parallel opposition to one another.

As used herein, the terms "subject" and "patient" refer to any animal, such as a dog, cat, bird, livestock, and particularly a mammal, preferably a human. In some instances, the subject is also a "user" (and thus the user is also the subject or patient).

As used herein, the term "sample" and "specimen" are used interchangeably, and in the broadest senses. In one sense, sample is meant to include a specimen or culture obtained from any source, as well as biological and environmental samples. Biological samples may be obtained from animals (including humans) and encompass fluids, solids, tissues, and gases. Biological samples include blood products, such as plasma, serum, stool, urine, and the like. Environmental samples include environmental material such as surface matter, soil, mud, sludge, biofilms, water, crystals, and industrial samples. Such examples are not however to be construed as limiting the sample types applicable to the present invention.

As used herein, the term "soft matter composition" is used without limitation to refer to any material or specimen of soft composition that can be sampled, e.g., by spooning or scooping, and encompasses, e.g., pastes, gels, soft solids, powders, foams, sludges, clays, tissues, etc.

As used herein, a "collection liquid" is a liquid in which to place a sample to preserve, stabilize, and otherwise maintain its integrity as a representative sample of the specimen from which the sample was taken. While not limited in the types of compositions that find use as collection liquids, examples of collection liquids are aqueous buffers optionally comprising a preservative and organic solvents such as acetonitrile.

As used herein, the term "half scoop" refers to a portion of a capsule that together with other scoop portions forms a complete scoop or sample capsule capable of, e.g., containing a sample. In some embodiments, two half-scoops that form a complete sample capsule are configured to comprise similar interior volumes, such that each half scoop encompasses approximately half of the volume of a complete sample capsule, while in some embodiments, half scoops may have significantly different interior volumes. In certain embodiments, a complete sample capsule or scoop is composed of more than two half scoop components.

The term "system" as used herein refers to a collection of articles for use for a particular purpose. In some embodiments, the articles comprise instructions for use, as information supplied on e.g., an article, on paper, or on recordable media (e.g., diskette, CD, etc.). In some embodiments, instructions direct a user to an online location, e.g., a website.

The term "kit" as used herein refers to a system that is packed or packaged, e.g., in a container such as a bag, box, pouch, etc., for convenient distribution to a recipient, e.g., through a distributor, a medical professional, or a pharmacy.

As used herein in reference to the shape of a capsule, the phrase "comprises a cylindrical portion" indicates that the capsule has the shape of a cylinder or of a modified cylinder, e.g., a cylinder with rounded ends, or other shapes of ends. Cylinder base and height dimensions applied to a modified cylinder refer to the cylindrical portion of the modified cylinder.

Embodiments of the Technology

Although the disclosure herein refers to certain illustrated embodiments, it is to be understood that these embodiments are presented by way of example and not by way of limitation.

With reference to FIGS. 1-13, embodiments of the collection device 100 and 200 provided herein comprise a frame 110, a slide 120, a first half-scoop 130, a second half-scoop 140, an actuator (e.g., a gear 150), and an ejector 170. The slide 120 fits into a hole 112 in the frame 110 such that the slide is moveably attached to the frame 110 in a way that allows the slide 120 to be translated along an axis coincident with the long major axes of both the frame 110 and slide 120.

The frame 110 comprises a scoop attachment 111 and the slide 120 comprises a scoop attachment 121. The half-scoop 130 and the half-scoop 140 are attached to the scoop attachments 111 and 121. The half-scoops 130 and 140 are attached such that they can be detached from the frame 110 and slide 120 by the user of the device. While not limited in the design of the scoop attachments 111 and 121 by which the half-scoops 130 and 140 are attached to the frame 110 and 120, FIGS. 1, 2, 3, and 5 show a configuration of the device using T-shaped scoop attachments 111 and 121 on the frame 110 and slide 120 that fit into T-shaped channels on the half-scoops 130 and 140. Any design that allows the secure attachment of the half-scoops 130 and 140 to the frame 110 and slide 120, while allowing the half-scoops 130 and 140 to be detached from the frame 110 and slide 120 by the user when desired, is encompassed by the present technology.

Figure 1:
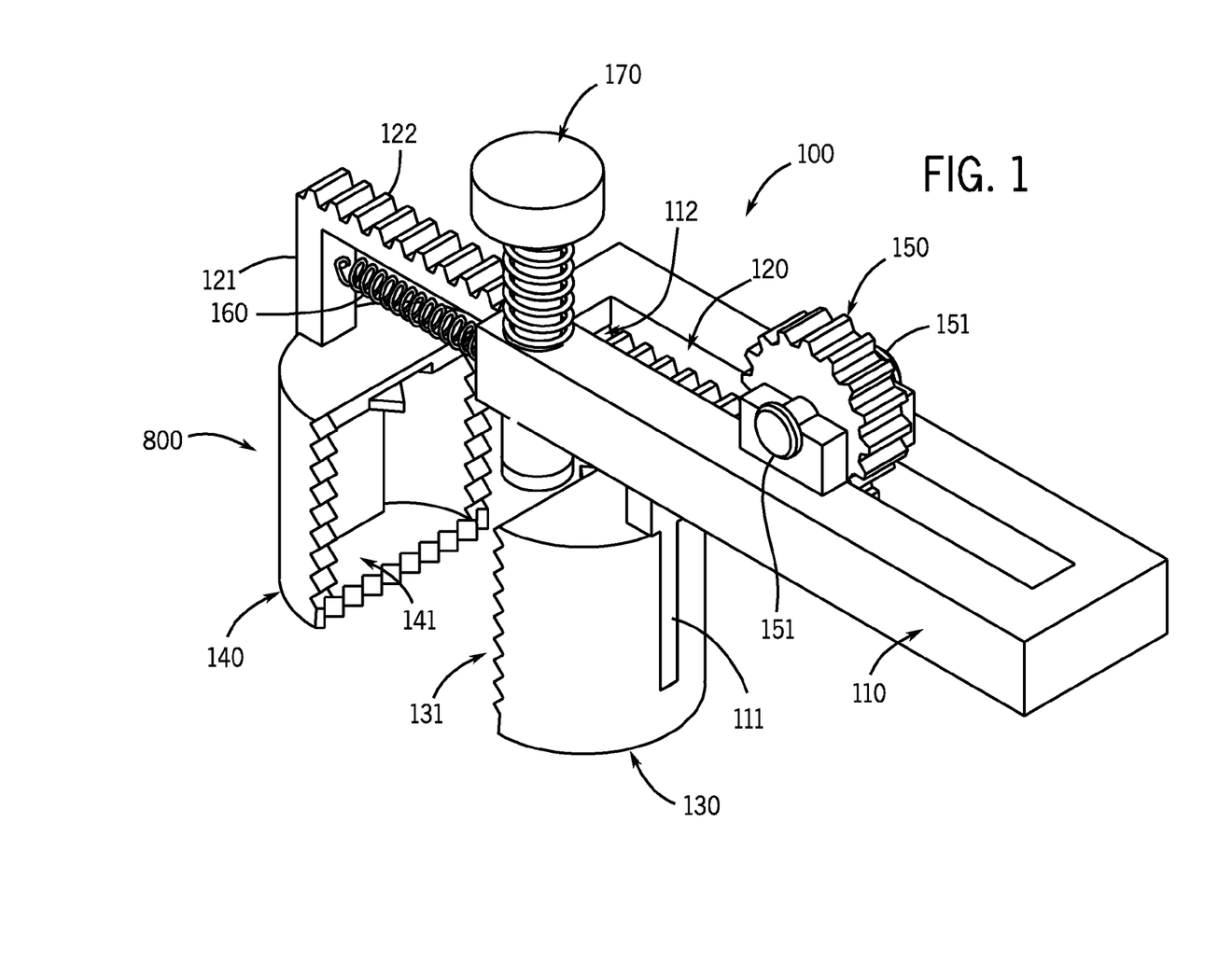
FIG. 1 is a drawing showing a perspective view of an embodiment of a stool sample collection device.
Figure 2:
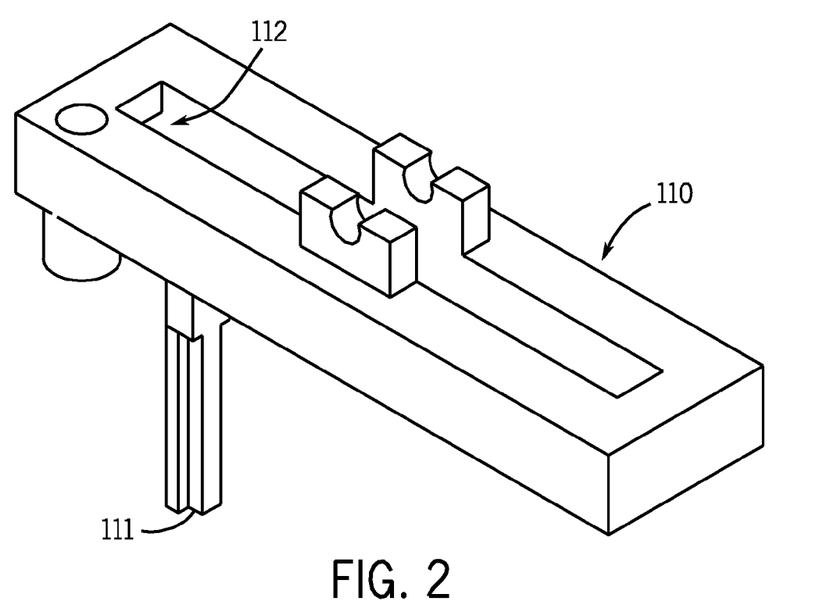
FIG. 2 is a drawing showing a perspective view of a frame piece for assembling the stool sample collection device shown in FIG. 1.
Figure 3:
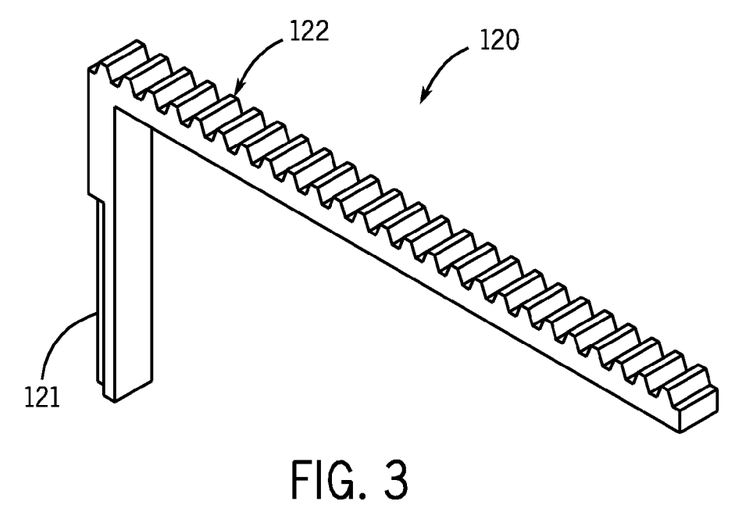
FIG. 3 is a drawing showing a perspective view of a slide piece for assembling the stool sample collection device shown in FIG. 1.
Figure 5:
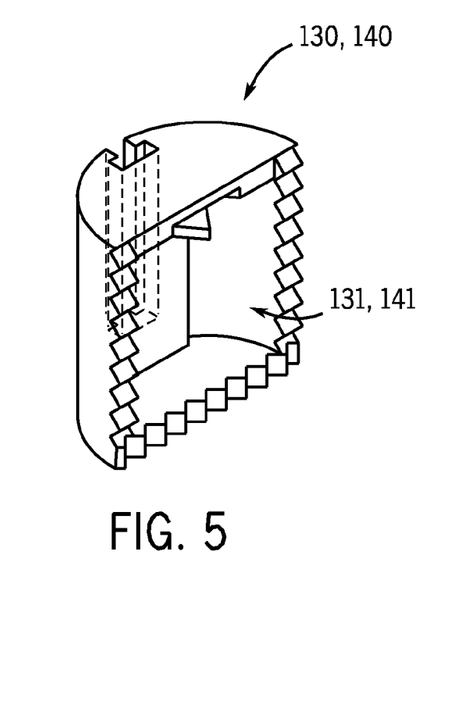
FIG. 5 is a drawing showing a perspective view of a half-scoop piece for assembling the stool sample collection device shown in FIG. 1.
Figure 6:
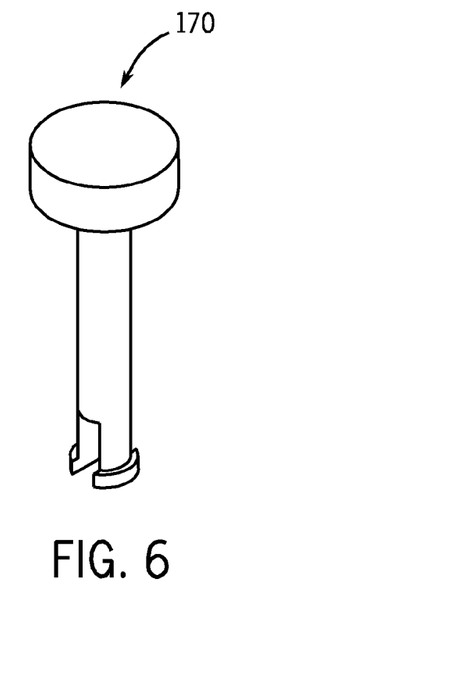
FIG. 6 is a drawing showing a perspective view of an ejector piece for assembling the stool sample collection device shown in FIG. 1.

As shown in FIGS. 1 and 5, each half-scoop 130 and 140 comprises a concave sample collection surface (e.g., 131 and 141). The half-scoops 130 and 140 are attached to the frame 110 and slide 120 such that the concave sample collection surfaces 131 and 141 are oriented toward each other in parallel opposition. That is, the concave sample collection surfaces 131 and 141 generally lie in parallel planes mutually normal to the long major translation axis of the frame 110 and slide 120. As the slide 120 is translated along this axis relative to the frame 110, the parallel opposition of the half-scoops 130 and 140 is maintained. Translating the slide 120 relative to the frame 110 thus results in translating the half-scoop 130 relative to the half-scoop 140, providing a mechanism to orient the half-scoops 130 and 140 around a sample and bring the half-scoops 130 and 140 together to encapsulate the sample. In some embodiments the half-scoops 130 and 140 comprise a hole (see, e.g., FIG. 13) to allow for the sample to drain or to allow air to escape when bringing the two half-scoops together. The holes are not limited in their size and shape and are any size and shape that allow for the collection of the sample and maintain the appropriate structural integrity of the half-scoops and the device. When present, the shapes and sizes of the holes are designed to be appropriate for the size, consistency, and type of sample for which the device is used.

Figure 7A:
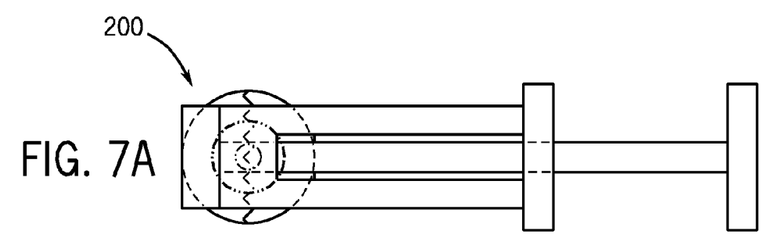
FIG. 7A is a drawing showing a top view of the closed device and FIG. 7B is a drawing showing a top view of the opened device.
Figure 7B:
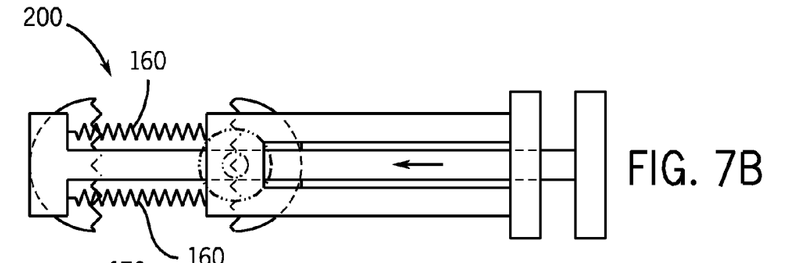
Figure 7C:
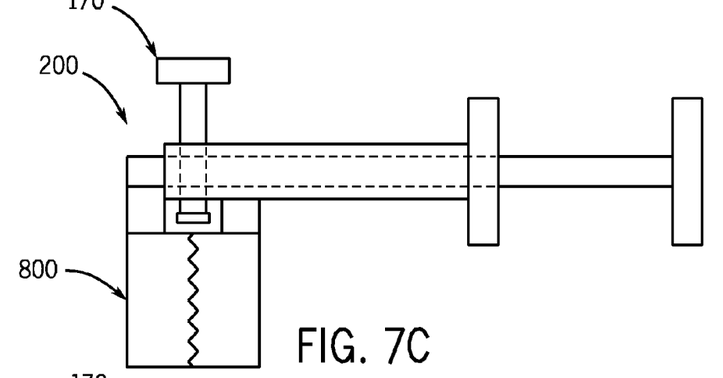
FIG. 7C is a drawing showing a side view of the closed device comprising an ejector and FIG. 7D is a drawing showing a side view of the opened device comprising an ejector.
Figure 7D:
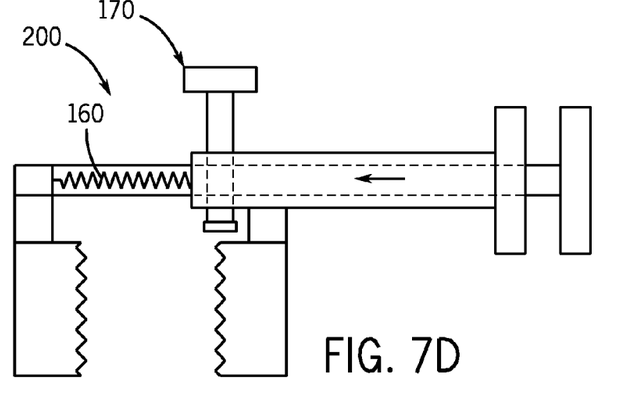
Figures 8A, 8B:
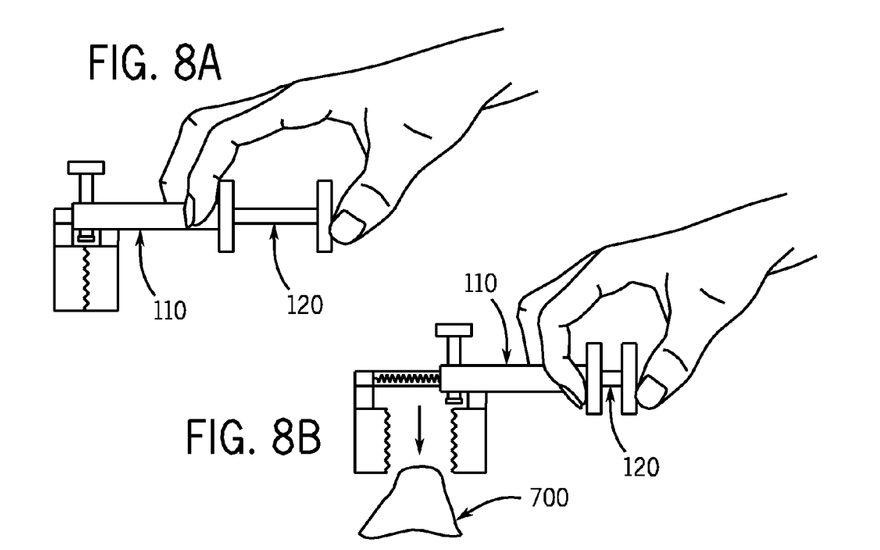
FIG. 8A shows the closed device held by a hand.
FIG. 8B shows a hand opening the device and positioning the half-scoop pieces around a stool specimen.
Figure 8C:
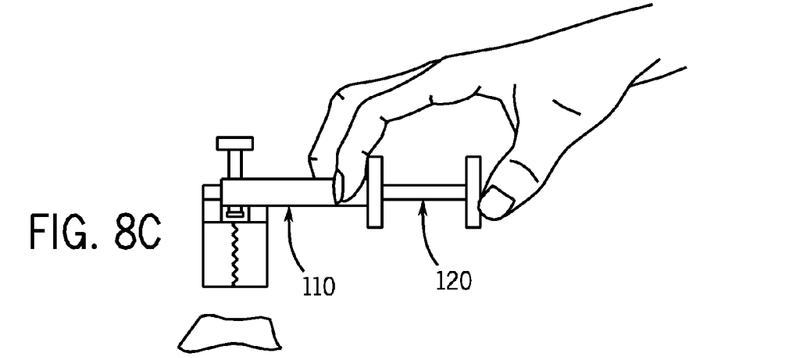
FIG. 8C shows the device with closed half-scoop pieces encapsulating a stool sample taken from the stool specimen.
Figure 8D:
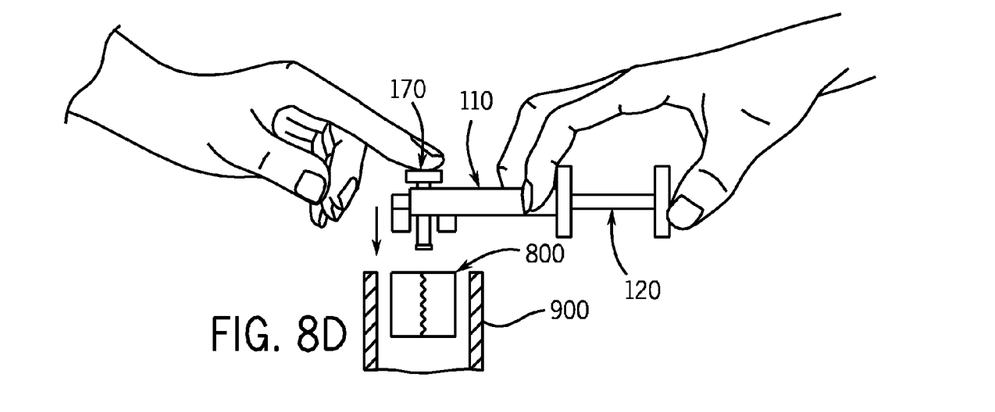
FIG. 8D shows use of the ejector to eject the closed half-scoop pieces and sample into a sample tube.

When the half-scoop 130 and the half-scoop 140 are brought together, the concave sample collection surfaces 131 and 141 form a detachable sample capsule 800 (see, e.g., FIGS. 1, 7C, and 8D). Accordingly, the half-scoops 130 and 140 can be brought together around a stool sample 700 (see, e.g., FIG. 8B) to encapsulate a defined and reproducible volume of stool within the detachable sample capsule 800. The detachable sample capsule 800 has a volume appropriate for the size of the sample required for testing. In addition, the detachable sample capsule 800 provides a way to produce a sample of reproducible volume from one sample preparation to the next. While the device is not limited in the volumes, weights, or masses of stool samples produced, in some embodiments, the detachable sample capsule has a volume of 1-10 cubic centimeters and thus is appropriate for providing a stool sample of approximately 1-10 grams. In some embodiments, a detachable sample capsule may contain more than 1 to 10 cubic centimeters, e.g., it may contain any useful volume operable by a body component, e.g., 11, 12, 13, 14, 15 . . . 20, 40, 60, 100, 150, 200, 300, or 500 cubic centimeters, and any fractional volume therebetween, or more. In certain preferred embodiments, the sample capsule has a volume of between about 4 and about 8 cubic centimeters. The detachable sample capsule 800 is of an appropriate size for depositing it and the enclosed sample into a sample tube or other vessel, e.g., a 50-cubic centimeter conical tube containing a stabilization buffer. A standard 50-cubic centimeter conical tube is approximately 115 millimeters long, has an outer diameter of approximately 29-30 millimeters, and has an inner diameter of approximately 28-29 millimeters. Accordingly, a detachable sample capsule 800 having a longest dimension no more than approximately 25-28 millimeters is an appropriate size to fit within or inside a standard 50-cubic centimeter conical tube.

Some embodiments provide that the half-scoops 130 and 140 are secured when brought together to form the detachable sample capsule 800. When secured, the detachable sample capsule 800 is maintained in a closed configuration when detached from the frame 110 and slide 120 so that the sample remains encapsulated within the detachable sample capsule 800, e.g., when removed from the frame 110 and slide 120 and deposited into a sample container. Securing the detachable sample capsule 800 protects the sample from exposure to environmental contaminants and protects the user and other sample handlers from exposure to the stool sample contained within the detachable sample capsule 800. While not limited in the means for securing the half-scoops 130 and 140, embodiments of the technology provide that a latch or clasp mechanism is used to secure one half-scoop to the other. For example, when one half-scoop 130 is brought together with the other half-scoop 140, the two half-scoops can snap together using a latching mechanism or a clasp to form a securely closed detachable sample capsule 800.

In some embodiments the detachable sample capsule 800 comprises a cap adapted to fit on a sample tube or other vessel. The cap securely seals the sample tube with the sample inside the tube. Without limiting the manner in which the cap seals the tube and to provide illustrative examples, in some embodiments the cap is threaded and screws onto the tube and in some embodiments the cap snaps onto the tube.

As shown in FIGS. 1, 7, and 8, embodiments of the device 100 and 200 comprise an ejector 170 (FIG. 6) used to detach the detachable sample capsule 800 from the frame 110 and slide 120. The ejector 170 is movably attached to the frame so that, when the half-scoop 130 and the half-scoop 140 are brought together, depressing the ejector 170 separates the detachable sample capsule 800 (comprising the half-scoop 130 and the half-scoop 140) from the scoop attachments 111 and 121 of the frame 110 and the slide 120 (see, e.g., FIGS. 8C and 8D), e.g., for depositing into a sample container 900 (e.g., a 50-cubic centimeter conical tube).

Figure 4:
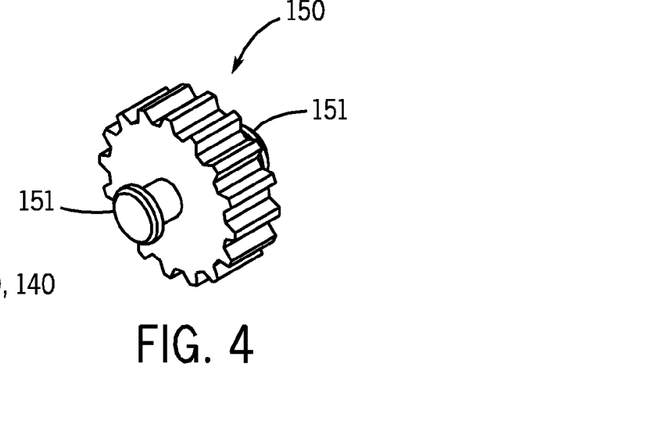
FIG. 4 is a drawing showing a perspective view of a gear with an axle for assembling the stool sample collection device shown in FIG. 1.

While the technology is not limited in the mechanism used to translate the slide 120 relative to the frame 110, thus bringing the half-scoops 130 and 140 together, embodiments of the device 100 and 200 are operated by manipulating an actuator or by directly manipulating the slide, e.g., using a grip and motion as would be used to manipulate a syringe (e.g., see FIG. 8). As shown in FIGS. 1 and 4, the actuator in some embodiments is a gear 150 comprising an axle 151. The gear 150 is rotationally attached to the frame 110 by the axle 151 such that the gear 150 engages gear teeth 122 on a surface of the slide 120 to form a rack and pinion mechanism. Rotating the gear 150 about the axle 151 in one direction causes the slide 120 to extend relative to the frame 110 and move the half-scoops 130 and 140 apart while maintaining their parallel opposition; rotating the gear 150 about the axle 151 in the other direction causes the slide 120 to retract relative to the frame 110 and move the half-scoops 130 and 140 together (and optionally secure them by a latch or clasp mechanism) while maintaining their parallel opposition. In some embodiments the actuator further comprises a lever, e.g., a lever attached to the gear such that manipulating the lever causes the gear to rotate. Also contemplated are other means by which the actuator engages and/or is operationally coupled to the slide, e.g., by an adhesive, rubber coating, or other substance or additional components providing a frictional coupling of the actuator and slide 120; by a string or ribbon; or by other mechanisms known by those in the art for converting rotational motion into linear motion. Also contemplated are embodiments using a source of electricity, a switch, and an electric motor or solenoid to translate the slide 120 relative to the frame 110.

In some embodiments, the design of the mechanism used to open and close the device 100 or 200 (i.e., to translate the slide 120 to move the half-scoops 130 and 140 together or apart) allows manipulation of the device by one hand, e.g., to capture a sample within the detachable sample capsule 800 and optionally deposit it into a sample container, e.g., a 50-cubic centimeter conical tube. Embodiments of the device provide that the portion of the device contacting the sample and the portion of the device contacted by the user are substantially separated to minimize exposure of the sample to the user and, conversely, to minimize exposure of the user to the sample.

In some embodiments, a spring 160 is attached to the frame 120 and slide 110. In some embodiments, the spring 160 pulls the half-scoops 130 and 140 together and thus force supplied by the user (e.g., by manipulating the actuator or the slide) is required to pull apart the half-scoops 130 and 140. In some embodiments, the spring 160 pulls the half-scoops 130 and 140 apart and thus force supplied by the user (e.g., by manipulating the actuator or the slide) is required to close and secure (e.g., by a latching or clasping mechanism) the half-scoops 130 and 140.

In some embodiments, the components (e.g., frame 110, slide 120, first half-scoop 130, second half-scoop 140, gear 150, and ejector 170) are made of a disposable material. For example, embodiments provide that the device 100 or 200 is made from plastic. In some embodiments, the first and second half-scoops 130 and 140 are made of a disposable material and the remaining components (e.g., frame 110, slide 120, gear 150, and ejector 170) are made of a reusable, sterilizable (e.g., autoclavable, bleach-resistant, ultraviolet radiation-resistant, gamma radiation-resistant, ethylene oxide-resistant) material (e.g., metal, plastic, and the like). Thus, in some embodiments, the first and second half-scoops 130 and 140 are replaceable parts adapted for use on a reusable device (e.g., comprising a frame 110, a slide 120, and other components required for use of the particular embodiment as provided herein). Reusable parts can be sterilized by methods known in the art appropriate for the materials used to produce the stool sampling device (e.g., autoclaving, bleach treatment, ultraviolet radiation, gamma radiation, ethylene oxide).

Figure 9:
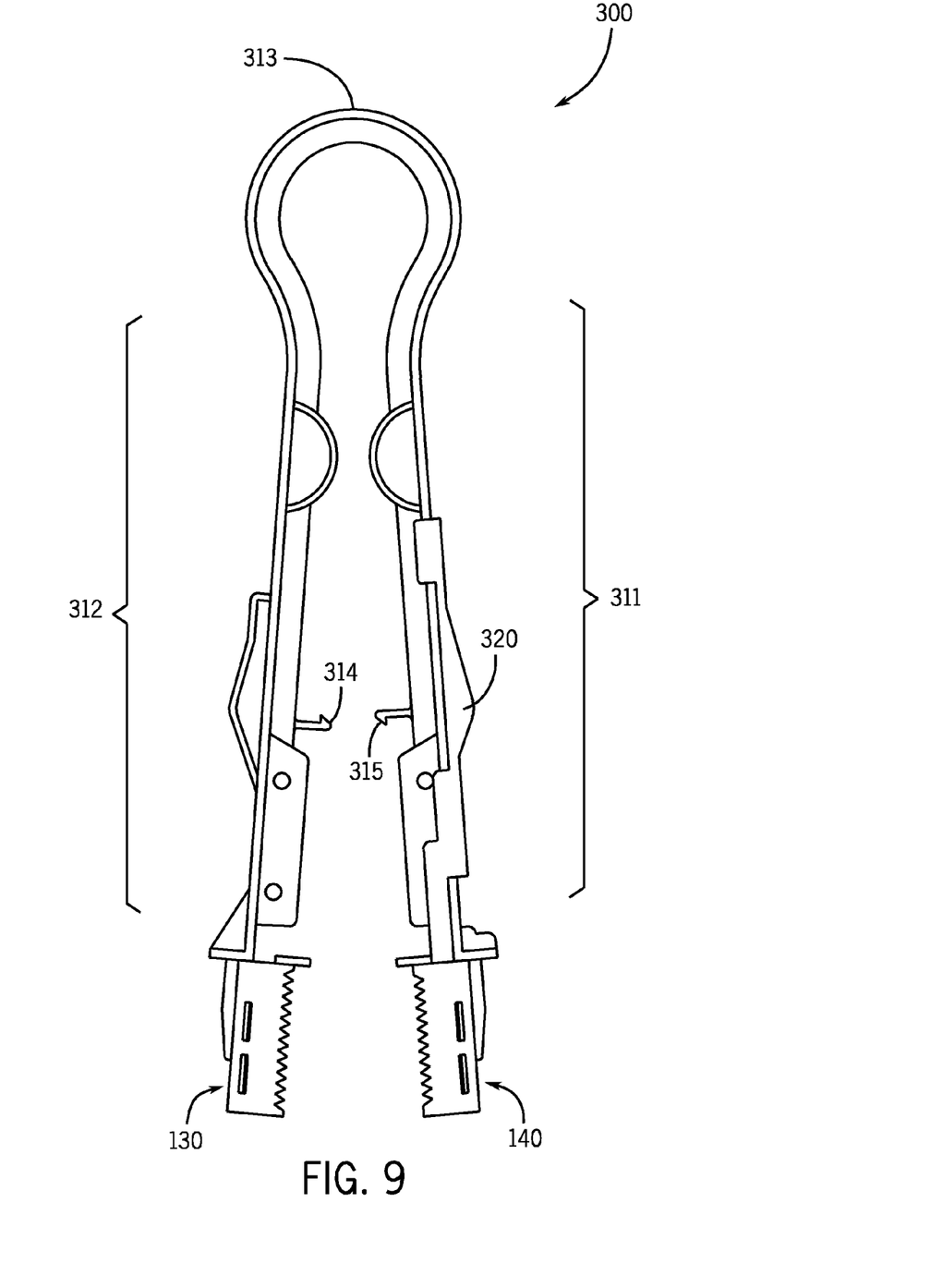
FIG. 9 is a drawing of an embodiment of the device comprising half-scoops/a detachable sample capsule attached to the body and comprising a slidable ejector.
Figure 11:
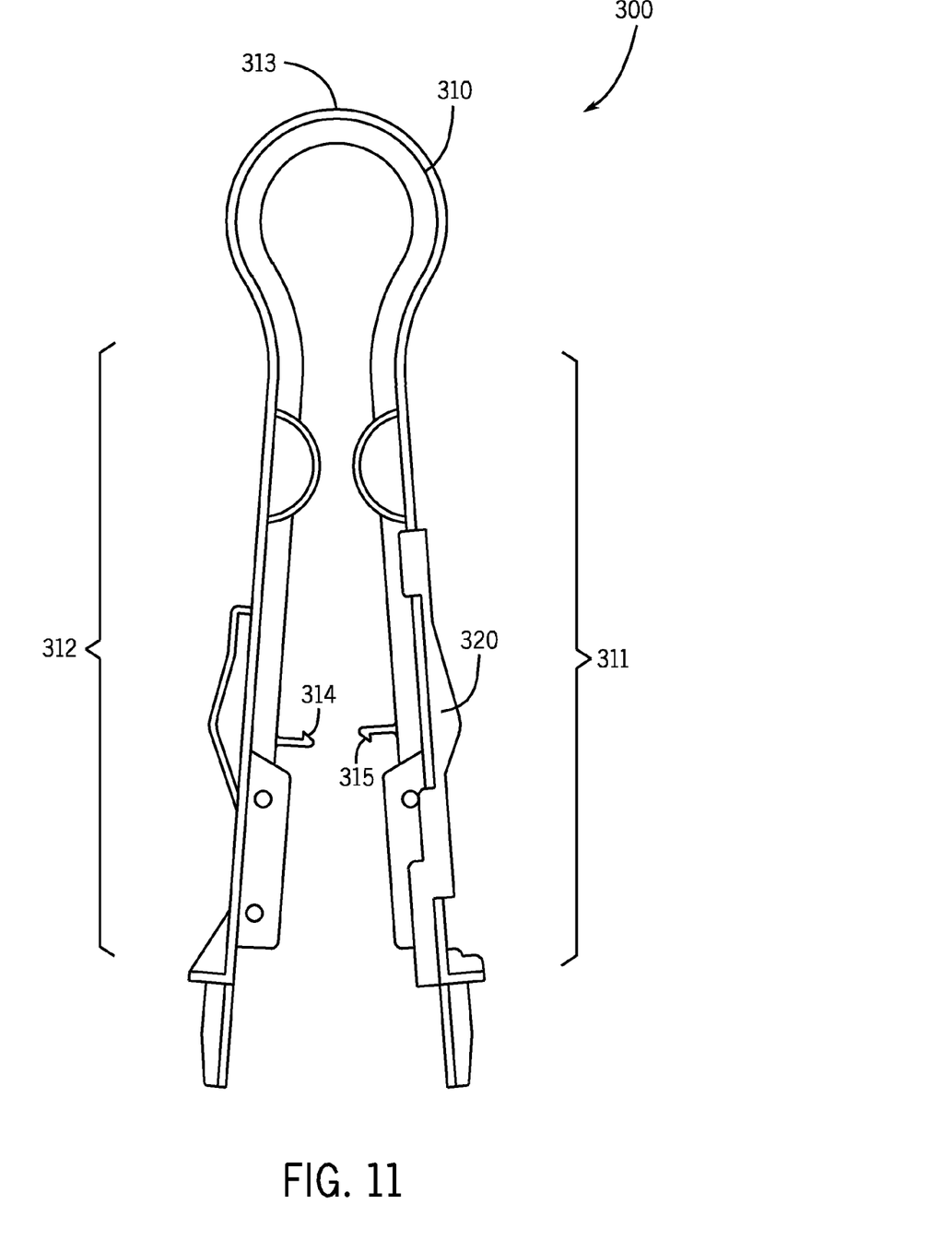
FIG. 11 is a drawing of an embodiment of the device shown in FIG. 9 with the half-scoops/detachable sample capsule detached from the body.

The exemplary embodiment 300 shown in FIGS. 9 and 11 is configured like a set of tongs or forceps. In this embodiment, the device comprises a body 310, an ejector 320, a first half-scoop 130, and a second half-scoop 140. The body 310 comprises a first operating member 311 and a second operating member 312. The first operating member 311 and the second operating member 312 are mechanically joined to form a fulcrum 313 such that the body 310, and in turn the device 300, is a third-class lever. The device 300 can be in an opened state (as shown in FIG. 9) or a closed state. In the closed state the half-scoop 130 and the half-scoop 140 form a detachable sample capsule 800. Manipulation of the ejector 320 by sliding it toward the distal end of the first operational member 311 or the second operational member 312 causes the detachable sample capsule 800 to detach from the body 310, allowing the user to deposit an encapsulated sample into a sample container. In some embodiments, the body 310 comprises a first latching mechanism 314 and a second latching mechanism 315 whereby the device 300 is secured in a closed state when the first operating member 311 and the second operating member 312 are brought together with enough force to cause the latching members 314 and 315 to engage. In the embodiment shown in FIGS. 9 and 11, the body 310 is a single piece that integrates the first operational member 311, the second operational member 312, and the fulcrum 313 into a single manufacture. The material has an appropriate springiness to maintain the device 300 in an open state when no user force is applied to the first operating member 311 and the second operating member 312 while allowing a user to apply a force to the first operating member 311 and the second operating member 312 to place the device 300 in a closed state and bring the half-scoop 130 and half-scoop 140 together to form the detachable sample capsule 800.

Figure 10:
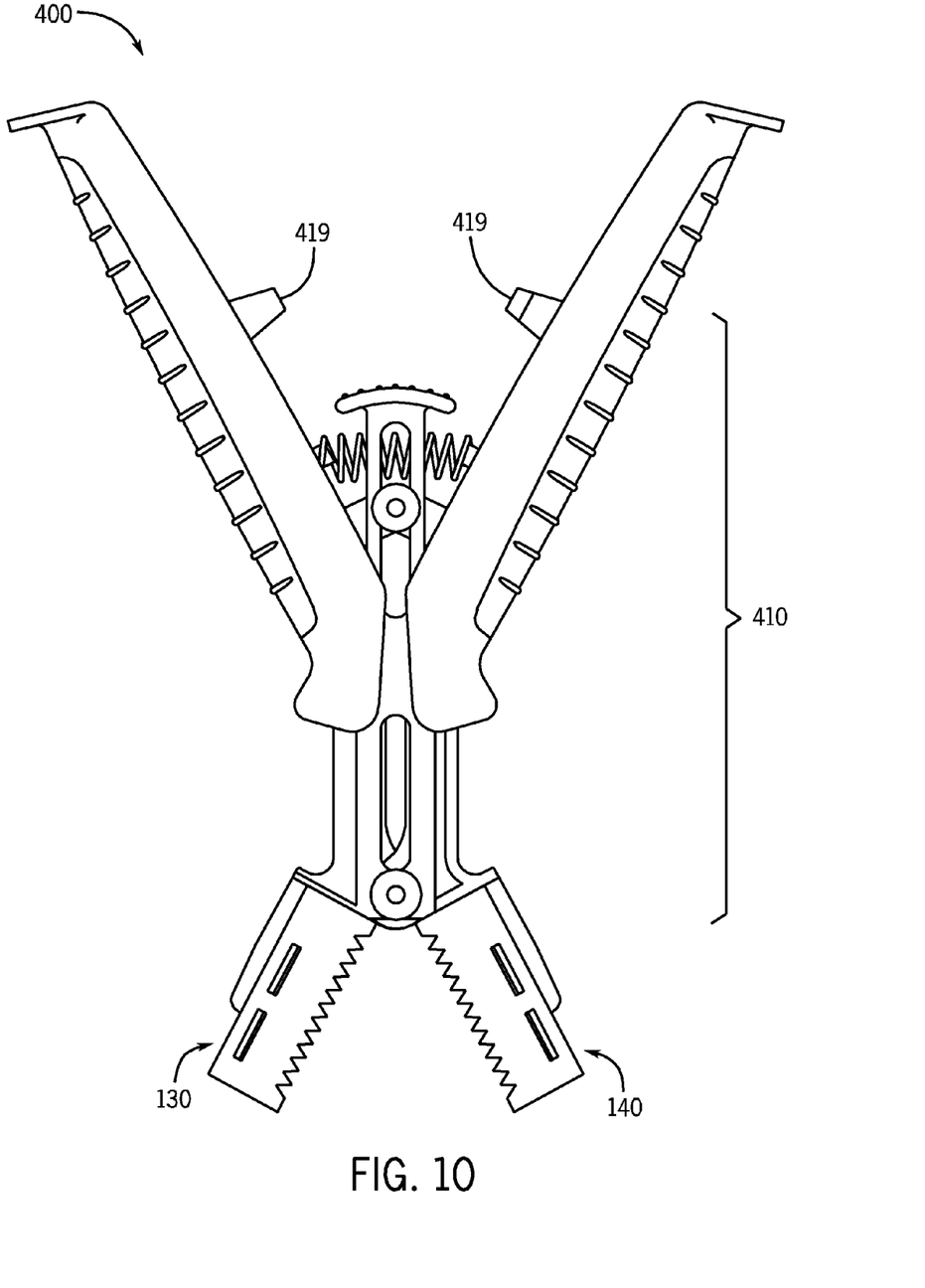
FIG. 10 is a drawing of an embodiment of the device comprising half-scoops/a detachable sample capsule attached to the body and comprising a slidable ejector.
Figure 12:
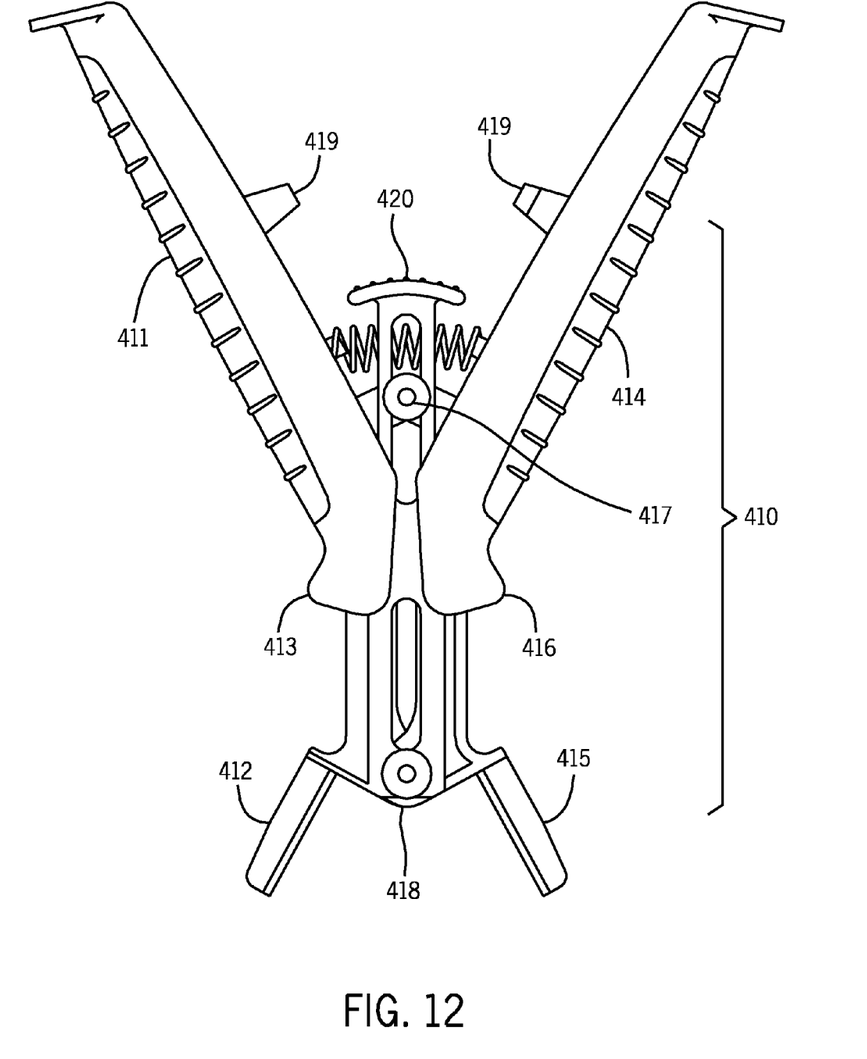
FIG. 12 is a drawing of an embodiment of the device shown in FIG. 10 with the half-scoops/a detachable sample capsule detached from the body.
Figure 13:
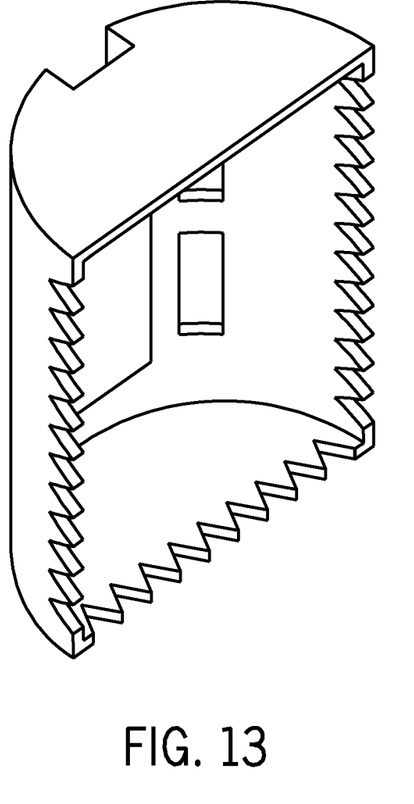
FIG. 13 is a drawing showing a perspective view of a half-scoop and the concave sample collection surface thereof.

The exemplary embodiment 400 shown in FIGS. 10 and 12 is configured as a compound lever (e.g., similar to that described in U.S. Pat. No. 3,636,954, incorporated herein by reference in its entirety for all purposes). In this embodiment, the device 400 comprises a body 410, an ejector 420, a first half-scoop 130, and a second half-scoop 140. The body 410 comprises a first compound lever and a second compound lever. The first compound lever comprises a first proximal operating member 411 and a first distal member 412 connected by a first joint 413. Similarly, the second compound lever comprises a second proximal operating member 414 and a second distal member 415 connected by a second joint 416. The first proximal operating member 411 and the second proximal operating member 414 are both first-class levers comprising the shared fulcrum 417. Similarly, the first distal member 412 and the second distal member 415 are both first-class levers comprising the shared fulcrum 418. The device 400 can be in an opened state (as shown in FIG. 10) or a closed state. In the closed state the half-scoop 130 and the half-scoop 140 form a detachable sample capsule 800. Manipulation of the ejector 420 by sliding it along an axis that bisects the longitudinal axes of the first proximal operating member 411 and the second proximal operating member 414 causes the detachable sample capsule 800 to detach from the body 410, allowing the user to deposit an encapsulated sample into a sample container. In some embodiments, the body 410 comprises a latching mechanism 419 whereby the device 400 is secured in a closed state when the first proximal operating member 411 and the second proximal operating member 414 are brought together with enough force to cause the latching mechanism to engage.

In the embodiments represented in FIGS. 9-12, the body (i.e., 310 and 410) can be manufactured from a disposable material (e.g., plastic, paper, cardboard) or from a reusable, sterilizable material (e.g., stainless steel). Likewise, the half-scoops 130 and 140 can be manufactured from a disposable material (e.g., plastic, paper, cardboard) or from a reusable, sterilizable material (e.g., stainless steel). Various combinations of materials are appropriate for different applications of the sampling devices provided herein. For example, for some applications, a user may desire to reuse the body for multiple samplings but not the half-scoops. In other applications, a user may desire the entire device to be disposable or reusable, and in some applications a user may wish to reuse the half-scoops but not the body (i.e., it is disposable).

The devices, methods, systems, and kits provided herein find use in obtaining a sample from a specimen. For example, embodiments of the device are used, for example, to obtain a food sample, an environmental sample, (e.g., soil, water, sand, sludge, biofilm, mud, etc.), a medical sample (e.g., stool, blood, tissue, hair, tumor, vomit, sputum), an industrial sample, etc. The devices are designed to achieve the appropriate mechanical force or mechanical advantage for collecting a sample and to comprise the appropriate materials to provide a sample from the specimen to be tested. For example, in some embodiments of the device, the device's design and materials are appropriate for sampling a material that has a soft composition (e.g., stool, bread dough, and the like) and thus requires little force to remove a sample therefrom. In other embodiments, the device's design and materials are appropriate for sampling a material that has a hard composition (e.g., dry soil, ice) and thus requires more force to remove a sample therefrom. In some embodiments, the materials are chosen to be chemically compatible with the sample collected. In some embodiments, the half-scoops are serrated or sharpened to facilitate their movement through the specimen in obtaining a sample, which is particularly useful for harder samples. One of skill in the art can choose a design and materials appropriate to provide and withstand the force required to obtain a sample in the particular sampling application wherein the device finds use.

Embodiments of the technology find use in obtaining a sample. For example, a user manipulates the device by placing the half-scoops on either side of a sample or specimen, moving the half-scoops to encapsulate a sample in the detachable sample capsule, and manipulating the device to detach the detachable sample capsule (containing the sample) from the body. It this way, a user can take a sample and deposit it in a sample container (e.g., a sample collection tube, e.g., a 50-milliliter conical tube). Embodiments of the device allow a user to take a sample and deposit the sample in a sample collection tube using one hand. In addition, embodiments of the device are designed to collect and provide a specific, reproducible, and uniform quantity of material from specimens of widely varying consistencies. The device is useful in collecting samples comprising materials or substances that stick or adhere to the materials of collection devices in that the sample capsule is detachable and thus use of the device does not require the user to touch or scrape the sample from the device after collection. The device is designed to be intuitive to use and furthermore allows a user to take a sample in the user's home without direct supervision being provided by a medical professional or one trained in clinical diagnostics.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in related fields (e.g., engineering, mechanics, materials science, or medical diagnostics) are intended to be within the scope of the following claims.

We claim:

1. A device for collecting a sample from a soft matter composition, comprising:
   a) a body; and
   b) a detachable sample capsule attached to the body, said detachable sample capsule comprising:
      i) a first half-scoop comprising a concave sample collection surface; and
      ii) a second half-scoop comprising a second sample collection surface opposed to said concave sample collection surface of said first half-scoop;
      wherein said detachable sample capsule is configured to move between an open state and a closed state, wherein the detachable sample capsule in said closed state comprises a sample collection space configured to enclose a sample;
   and
   c) an ejector mechanically connected to said body, said ejector configured to detach said detachable sample capsule from said body when said detachable sample capsule is in a closed state.

2. The device of claim 1, wherein said second sample collection surface comprises a second concave sample collection surface.

3. The device of claim 1, wherein:
   a) when said detachable sample capsule is in said open state, said body is in a first state and said first half-scoop is separated from said second half-scoop; and
   b) when said detachable sample capsule is in said closed state, said body is in a second state and said first half-scoop is in contact with said second half-scoop such that said concave sample collection surface of said first half-scoop and said second sample collection surface of said second half-scoop form said sample collection space.

4. A method of collecting a sample from a soft matter composition, comprising the steps of:
   1) positioning a device according to claim 2 in an open state, so that said first half-scoop is placed on one side of a portion of said soft matter composition and the second half-scoop is placed on another side of said portion of said soft matter composition;
   2) moving said device into said closed state, wherein said a sample of said soft matter composition is encapsulated in said sample collection space; and
   3) actuating said ejector, wherein said detachable sample capsule is ejected from said body of said device.

5. The method of claim 4, wherein said detachable sample capsule is ejected into a sample container.

6. The method of claim 4, wherein said device encapsulates a sample of said soft matter composition having a mass between about 1 and about 10 grams.

7. The method of claim 4, wherein said soft matter composition is a food composition.

8. The method of claim 4, wherein said soft matter composition is stool.

9. The device of claim 1, wherein said sample collection space has a volume between about 0.5 to 10 cubic centimeters.

10. A system for collecting a sample from a soft matter composition, comprising:
   (a) a device according to claim 1; and
   (b) a sample container;
      wherein the sample container is configured to contain the detachable sample capsule of said device in a closed and detached state.

11. The system of claim 10, further comprising a collection fluid.

12. The system of claim 11, wherein said collection fluid is contained in said sample container.

13. The system of claim 10, further comprising instructions for use of the system.

14. The system of claim 10, further comprising a receptacle configured to collect an entire specimen of said soft matter composition from a user.

15. A kit for collecting a sample of a soft matter composition, said kit comprising the system of claim 10.

16. The device of claim 3, further comprising a first clasp component and a second clasp component, wherein said first clasp component and said second clasp component engage to secure said article a state wherein said detachable sample capsule is in said closed state.

* * * * *